United States Patent [19]

Vilsmeier et al.

[11] Patent Number: 5,702,406
[45] Date of Patent: Dec. 30, 1997

[54] DEVICE FOR NONINVASIVE STEREOTACTIC IMMOBILIZATION IN REPRODUCIBLE POSITION

[75] Inventors: Stefan Vilsmeier, Poing; Stefan Lippstreu, Markt Schwaben; Michael Bertram, Heimstetten, all of Germany

[73] Assignee: BrainLAB Med. Computersysteme GmbB, Germany

[21] Appl. No.: 526,626

[22] Filed: Sep. 11, 1995

[30] Foreign Application Priority Data

Sep. 15, 1994 [DE] Germany ............ P 44 32 891.5

[51] Int. Cl.6 .................................. A61B 19/00
[52] U.S. Cl. .................. 606/130; 128/845; 128/857
[58] Field of Search .................. 606/130; 128/206.16, 128/206.17, 206.19, 653.1, 653.2, 653.5, 845, 857; 5/622

[56] References Cited

U.S. PATENT DOCUMENTS

| | | | |
|---|---|---|---|
| 2,056,753 | 4/1936 | Wagner | 128/206.19 |
| 2,149,067 | 2/1939 | Otero | 128/206.16 |
| 4,657,010 | 4/1987 | Wright | 128/206.16 |
| 5,370,117 | 12/1994 | McLaurin, Jr. | 128/653.1 |
| 5,464,411 | 11/1995 | Schulte et al. | 606/130 |

*Primary Examiner*—Mickey Yu
*Assistant Examiner*—Justine R. Yu
*Attorney, Agent, or Firm*—Dann, Dorfman, Herrell and Skillman, P.C.

[57] ABSTRACT

The present invention pertains to a device for noninvasive, stereotactic immobilization in reproducible position with a head ring providing a firm reference system, a mask consisting of several parts attached to the head ring. The mask is individually adapted to the anatomical contours of a patient, and has mask parts connected with one another as well as with the reference system. The connections enable adjusting the relative position of the mask parts to one another.

10 Claims, 5 Drawing Sheets

DEVICE FOR NONINVASIVE STEREOTACTIC IMMOBILIZATION IN REPRODUCIBLE POSITION

FIELD OF THE INVENTION

The present invention pertains to a device for noninvasive stereotactic immobilization in reproducible position.

BACKGROUND OF THE INVENTION

For the radiation therapy of patients, in whom, for example, a tumor was diagnosed in the head by means of computerized tomography, it is necessary to immobilize the head of the patient relative to a reference system that is already secured in position during the tomography. For this purpose, a stable head ring is, in general, already attached to the patient's head before the computerized tomography. The location of the tumor with regard to this head ring, which serves as a reference system, can then be determined during the computerized tomography. This head ring, on which various instruments may be arranged, must either remain on the head of the patient or be arranged there again in reproducible position for further therapy.

In current therapeutic practice, it is possible for head rings to remain on the head due to the fact that the head ring is immovably fixed by means of pins which penetrate into the head of the patient from the outside. As a disadvantage, the patient must wear the head ring fixed in this manner for the entire time in the case of longer periods of therapy, which can be associated with pain, at any rate, however, with discomfort. Also, it is not always possible, e.g., in the case of small children, to use this type of attachment of the head ring, since damage to the bone structure may occur.

To avoid the problems mentioned above, an attempt was made to create a noninvasive, but reproducible fixation system for stereotactic radiation therapy. In this system, a mask made of dressing material was applied around the head of the patient, whereby the dressing material was then fixed by means of a spray to the individual contours of the patient. In this case, it was necessary to give the patient an opportunity to breathe by means of special devices, e.g., tubes, while the mask was being applied and fixed. After the mask hardened, it was sawed along the sides of the head and over the top of the head into a front part and a rear front, and both halves were provided with a joint on the one side and a closing mechanism on the other side and were associated with a reference system, e.g, a head ring. Also, after the mask hardened and it was removed from the patient, openings for seeing and breathing could be inserted into the mask.

As a result, a noninvasive system for stereotactic immobilization that can be applied and removed had been created.

In the first place, a great disadvantage of this system concerns the only moderately accurate reproducibility of the position of the head ring to be set by means of the mask. Patients, who undergo a treatment with this mask spread out over a period of, e.g., several days, do not require the same spacing of the mask parts on each day of the treatment. This spatial requirement or the pressure requirement on the mask may change depending on the time of day, the state of health, the condition of the patient, or similar circumstances. This change cannot result from the mask produced as described above, since the spacings between its parts are determined in the state, in which it was first applied and joined. Thus, if the face of the patient swells up, such a mask may lead to unpleasant feelings of difficult breathing in him. If the face of the patient should appear to have an overall smaller spatial requirement on a later day of treatment, then there is a risk that the above-described mask will be loose, and the accuracy of the treatments to be carried out with it will no longer be guaranteed.

Another great disadvantage of the mask designed according to the above state of the art concerns the fact that its acceptance by the patient is very poor. Already during the first application, the patient must breathe by means of breathing aids, e.g., air tubes, especially because even the lower jaw must be inserted into the mask in order to achieve a satisfactory firmness. Even the eyes are covered during the preparation procedure. All the above can lead to the patient feeling claustrophobic, especially because this patient must remain in one position as much as possible during the hardening time.

Other disadvantages concern especially the relatively poor stability of this mask and the fact that, based on its brittle properties, it is relatively susceptible to impacts of any kind.

SUMMARY OF THE INVENTION

The task of the present invention is to create a device for noninvasive, stereotactic immobilization in reproducible position, which no longer has the above-described disadvantages of the state of the art. Such a device, which is readily accepted by the patient and can be utilized with high accuracy, should especially be proposed.

This task is solved by an improved device which is designed as a mask having parts conforming to the anatomical contour of a patient and having connections for adjusting the relative positions of the mask parts.

The special advantage of the mask designed according to the present invention lies in the fact that, since the mask is provided, on its connection means, with means for adjusting the relative position of the mask parts to one another, a possibility is created for following the changing pressure requirement of the head of the patient. As a result, the connection means for the mask parts is simultaneously a means for adjusting the pressure for the mask. Therefore, by reducing the mask pressure, e.g., it can be prevented that a patient cannot, therefore, be treated with sufficient accuracy because the head ring fixed by the mask is not fixed rigidly enough in its position. Unpleasant feelings of difficult breathing can also be prevented in patients who temporarily have a greater spatial requirement by the fact that the mask is, all in all, enlarged via the adjustment means. Therefore, the mask will be accepted by the patient at any time and thus will make an accurate treatment possible.

The mask parts should advantageously consist of a thermoplastic material. The processing of this material is especially simple, since it can easily be adapted to the contours of the head of the patient after it has been heated, e.g., in warm water, and it hardens while cooling.

Such materials can be selected such that they do not adhere to the patient's skin and hair, which improves the acceptance and the later detachability of the mask after hardening. In addition, such thermoplastic materials, in the hardened state, are hard enough to guarantee the reproducibility of the position of the head ring; however, they still have a sufficient elasticity to withstand even hard impacts of any kind and to return to their original position after elastic deformation.

Due to the excellent stiffness of the thermoplastic materials in the mask according to the present invention, there is no longer the need to integrate the lower jaw part, so that the patient can breathe freely at least through the mouth already when the mask is applied.

It is possible to form the mask parts at least partially from a thermoplastic material that is designed as permeable to air. Such plastic mats can be perforated and/or have a netlike design, and they can make it possible for the patient to additionally breathe through his nose and to see through the perforations or the gaps in the net, with the mask still being sufficiently stable during the application. Thus, the acceptance and the comfort during the application and wearing of the mask are considerably increased, whereby the state of claustrophobia can be ruled out to a large extent.

In a preferred embodiment of the present invention, the mask has a rear part and a multilayered front part, whereby the back of the head of the patient is supported by the rear part, while the patient is preset in position by means of a first layer of the front part, e.g., by means of strips of thermoplastic material, and is later completely immobilized by another layer, which may consist, e.g., of a mat of the material.

In the embodiment discussed above, it is also possible for a front mask part of one layer to have a support section made of a thermoplastic material, which accommodates the root of the nose of the patient. This section may consist of a heated, softened plastic and, for example, may be connected with an upper strip, which presets the patient's forehead in position. The other end of this Support for the root of the nose is thereafter molded to the root of the nose of the patient and thus forms an individually adapted, additional means of support and alignment for the mask.

The mask parts, which would cover the area of the mouth of the patient, are preferably left out at these points, so that this patient can breathe easily through the mouth during the application and wearing of the mask.

In another aspect of the device according to the present invention, the connection means for connecting the mask parts with one another as well as with the reference system consists of two groups of strips, which are arranged vertically to the side of the head of the patient, in which groups of strips one strip is mechanically connected with the reference system. The arrangement of the groups of strips to the side of the head makes it possible to shape the mask for the first time without problems, while the patient lies on the back of his head, and to reapply the mask in the case of further treatment likewise without problems.

The device according to the present invention can preferably be designed such that the mask parts have strips attached to their longitudinal edges, which strips are joined and attached to the connecting strip with the reference system during the putting together and during the first and repeated application of the mask, whereby additional spacing strips of various widths can be placed between them, and by their variation in width, the relative position of the mask parts can be adjusted to one another. An especially simple, applicable implementation of the principle of the mask, which is changeable under pressure, now arises here. The strips located on the mask parts are attached to the side edges adjacent to the longitudinal sides of the head and can be simply applied flat to a means of connecting with the reference system, which means are provided, e.g., with guide rails. By the connection means having a suitable design, it does not matter here how many parts the mask consists of, such that a high possibility of variation with regard to the design of the mask is achieved here. The pressure variation of the mask, i.e., the adjustability, is achieved by means of spacing strips, which can be inserted among the strips located on the mask parts. These spacing strips can have different widths and thus provide the possibility of adjusting the pressure for the mask, which is very accurate and easy to use.

This implementation possibility presents an especially favorable form of connecting the strips connected with the reference system with the strips arranged on the mask parts, as well as with the spacing strips for a tight fitting of the mask. The groups of strips can be held together securely and can be rapidly detached by means of clamps, which, e.g., are seated in grooves that are formed in all the connecting strips and which hold the strips together from the outside. In this case, it is advantageous to provide a clamp both above and below for each group of strips, in which case the clamps can be provided in various designs and are each adapted to the width of the spacing strips. The outer strips can also have auxiliary aids, such as, e.g., recesses for holding the clamps. If the need should arise to rapidly remove the mask for any reason, then this can occur simply by the fact that the clamps are rapidly pulled off, by means of which the front mask parts are pulled off towards the front in a simple manner.

A detachable support for the back of the head, which is also at least partially made of a plastic material, can be arranged on the reference system for the support of the back of the head and for further stabilization of the mask position.

In addition, the present invention pertains to a set of mask parts, which can be especially used with an above-described device according to the present invention for noninvasive, stereotactic immobilization in reproducible position.

Using thermoplastic materials for the fixation of body parts of patients is known. These fixation materials are, in general, softened in warm water and then pulled from the front over the head of the patient to be attached to the side parts, e.g., on a plate. The patient is thereby immobilized, whereby this immobilization has an accuracy with a deviation of 3 to 5 mm according to use. As a disadvantage, the immobilization system achieved in this manner is not generally used for procedures of radiation therapy due to the poor accuracy when it is used again, in which procedures accuracies with deviations of less than 1.5 mm are required.

Therefore, another task of the present invention is to make available a set of mask parts, in which it is guaranteed that a mask can be created, which offers reproducible immobilization of a patient with sufficient accuracy and which can be arranged on a reference system for radiation therapy, especially when using the device according to the present invention.

This task is solved by the set of mask parts, which is designed to accommodate relative adjustment of the positions of the mask parts. The arrangement of a section for the root of the nose or the bridge of the nose of the patient gives the resulting mask a very good stability and a good reference point for the reproducibility of the position of the parts attached to the mask. This is especially based on the fact that the bone structure in the area of the root of the nose lies directly under the skin and thus is available as a hard contour. The mask parts are, according to the present invention, provided, on the side edges which come to lie in the vertical position, with connecting parts for connecting with one another as well as with a reference system.

In addition, adjusting means are provided, with which the relative positions of the mask parts can be adjusted to one another. Thus, the already previously known advantages with regard to the adjustability of the pressure of the mask become noticeable. The set of mask parts may be suitable for all patients based on its thermoplastic deformability as the unit size and thus can be produced and marketed in a cost-favorable manner. This has a positive effect on the use, e.g., of the device according to the present invention for several patients, since, according to the adjustment of the mask, one head ring can be used for several masks.

The set of mask parts according to the present invention is preferably designed such that the connecting parts consists of strips having the same length for all mask parts, and the adjusting means are made from spacing strips of various widths. A system for adjusting the pressure for the mask is again made possible here, which is simple to produce and arrange, and in which the strips permit a very simple assembly of the mask with, e.g., a head ring, by placing them one on top of another together with the spacing strips and a connecting strip.

The strips can be connected mechanically, e.g., by means of riveting, on the vertical side edges of the mask parts, by means of which an especially secure hold is obtained. However, it is also possible to glue the side parts together with the strips.

BRIEF DESCRIPTION OF THE DRAWINGS

The present invention is now described in detail by means of an exemplary embodiment with reference to the attached pages of figures, in which.

DESCRIPTION OF THE PREFERRED EMBODIMENTS

Figure 1A:
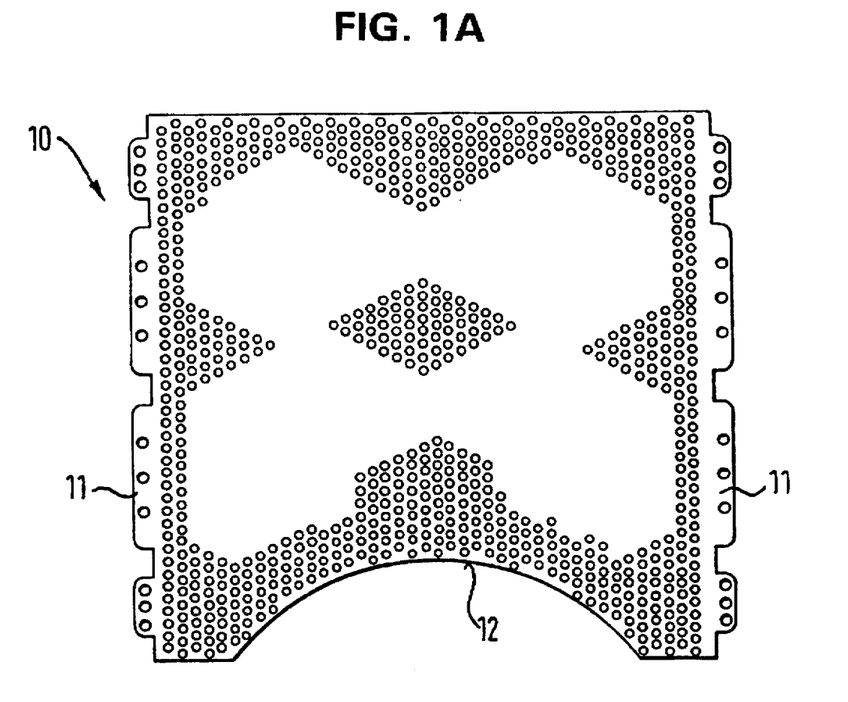
FIG. 1A shows, on the top, a front or rear mask part made of thermoplastic material in the initial state.
Figure 2A:
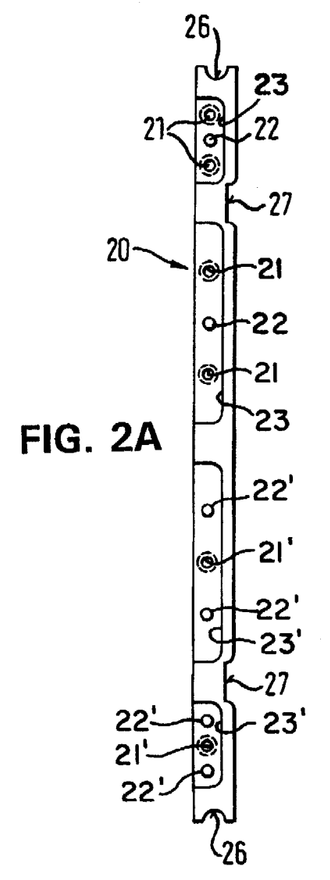
FIG. 2A shows a top view of a strip to be arranged on the edges of the mask parts.
Figure 2B:
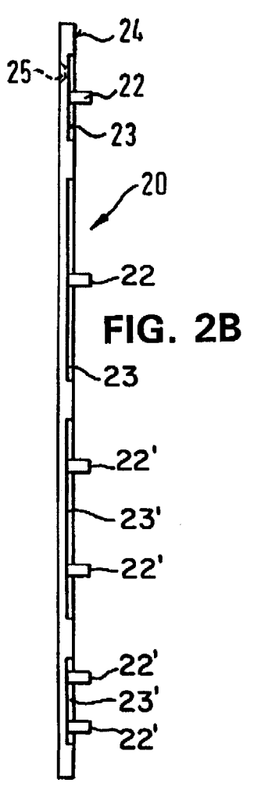
FIG. 2B shows a side view of the strip shown in FIG. 2A.

FIG. 1A shows a front or rear mask part 10 which is made of a thermoplastic material and is perforated in a netlike manner in the present exemplary embodiment. On the lower edge of this mask part is provided a recess 12, which provides an opening for the mouth area of the patient, when used as the front part of the mask, and an opening for the neck area of the patient when used as the rear part. On the left and right longitudinal sides of the mask part 10, attachment extensions 11 are provided over essentially the entire length for arranging the strips 20 (FIG. 2). In this embodiment, the attachment extensions 11 are provided with holes, which permit their later rigid connection, e.g., by means of riveting, with the strips 20 (shown in FIGS. 2A and 2B).

Figure 1B:
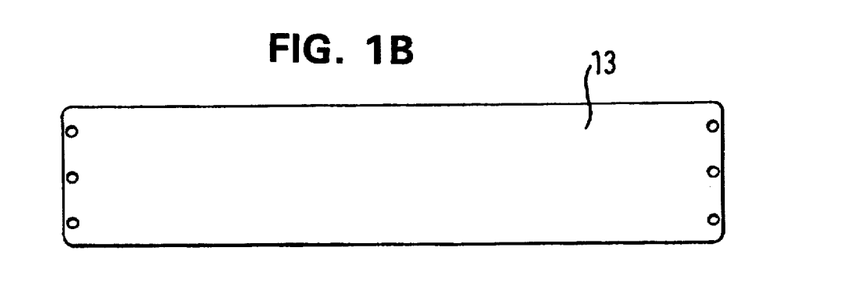
FIG. 1B shows a fixation strip for the forehead area of the patient made of thermoplastic material in the initial state.

FIG. 1B shows a fixation strip 13 made of thermoplastic material, which is used to temporarily immobilize the forehead area of the patient using the mask according to the present invention. The fixation strip 13 is not perforated since it is not placed over the eyes or the mouth of the patient, and again, it has, on its side edges to the left and to the right, holes for connection with a strip 20 of the means of connection with a reference system.

Figure 1C:
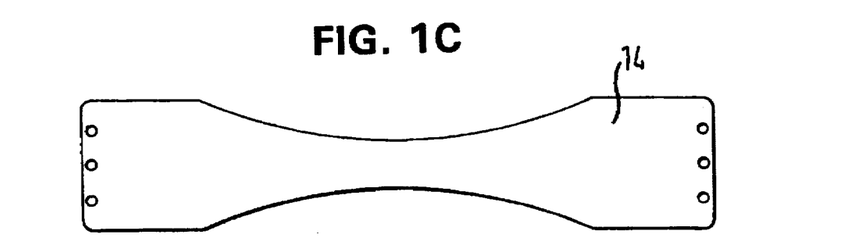
FIG. 1C shows a fixation strip for the upper jaw area of the patient made of thermoplastic material in the initial state, whereby holes for the attachment of strips are provided on the side edges of the mask parts shown.

FIG. 1C shows a fixation strip 14 for the upper jaw area of a patient. On its side edges, this fixation strip also has holes for the attachment of a strip 20 and, in its middle area, which comes to lie above the upper lip of the patient, is tapered so as not to protrude into the mouth area of the patient.

Figure 3A:
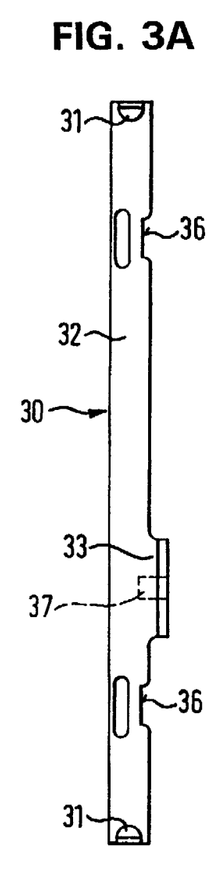
FIG. 3A shows a top view of a connecting strip, on which the strips in FIG. 2 can be arranged and which is connected with a reference system.
Figure 3B:
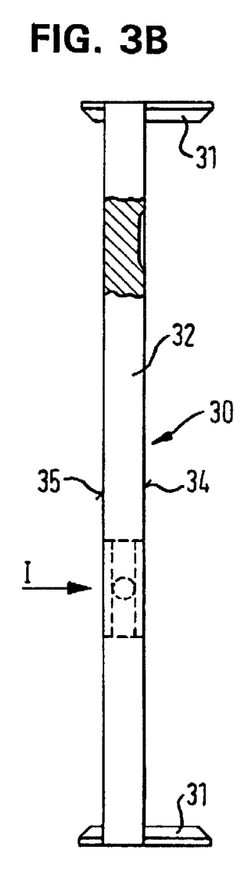
FIG. 3B shows a side view of the connecting strip shown in FIG. 3A.
Figure 6:
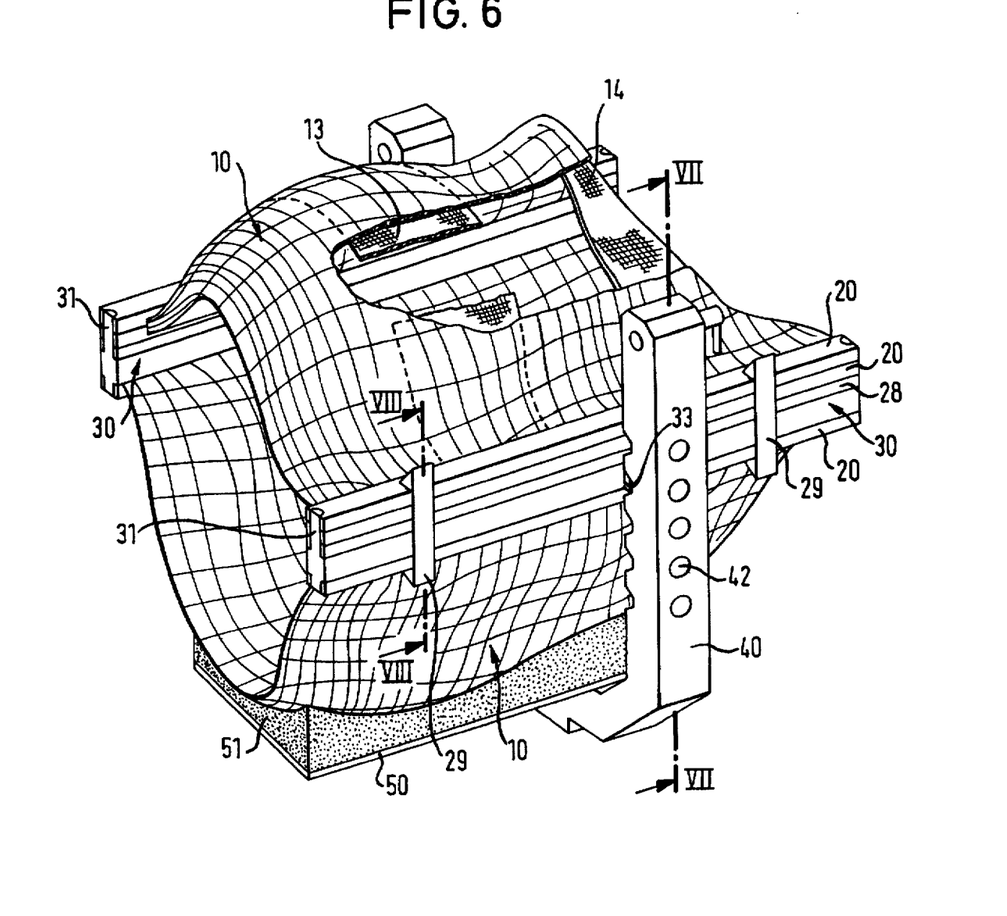
FIG. 6 shows a perspective view of the entire device according to the present invention.
Figure 7:
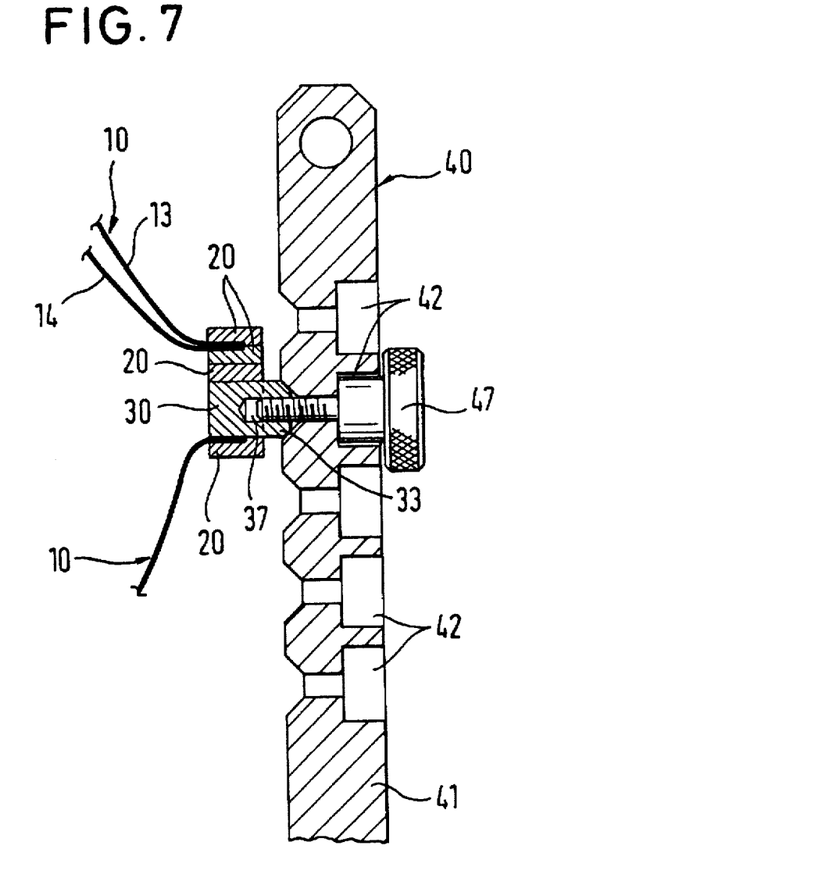
FIG. 7 is a sectional view taken on the line VII—VII of FIG. 6.
Figure 8:
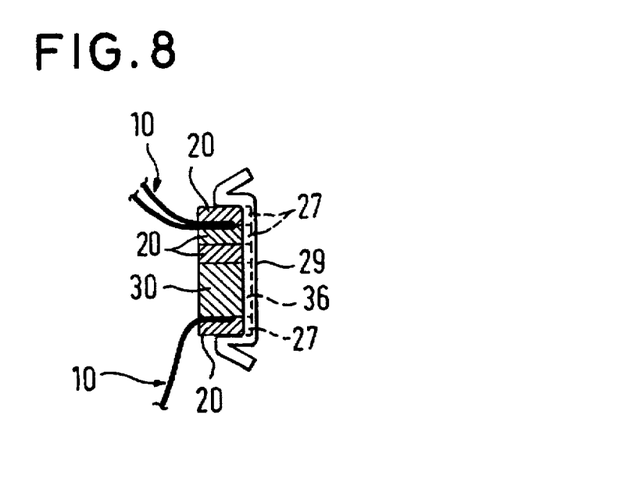
FIG. 8 is a sectional view taken on the lines VIII—VIII of FIG. 6.

The strip 20 shown in FIGS. 2A and 2B is applied to the respective mask parts even before the mask is placed on the patient. The strip 20 shown here is designed for arranging on a front part or rear part 10. For this purpose, it has connecting holes 21, which pass through their wider side, as well as connecting pins rivets 22, which stick out from it. The position of the holes 21 and the pins 22 corresponds to the position of the holes of the attachment extension 11 of the mask part 10. Two strips 20 are applied by means of the connecting pins 22 and the left and right attachment extension 11 of a mask part 10, and they are riveted, i.e., rigidly connected, with these through the connecting holes 22. In FIG. 2B recesses 23 are arranged at the points, where the connecting pins 22 and connecting holes 21 are arranged. When the pins are inserted through the holes in the marginal edges 11 of the part 10 and are riveted or shortened, attention must be paid that no attachment part protrudes beyond the surface 24 of the strip 20, so that it is later guaranteed that the strips lie flat on top of one another. When the parts 10, 13 and 14 are captured between two strips 20, as shown in FIG. 6, one of the strips 20 may be inverted top-to-bottom to enable the parts 10, 13 and 14 to be captured between the two strips. As shown in FIGS. 2A and 2B, the spacings between the pairs and holes are the same above and below the longitudinal mid-point of each strip, but with the sequence of pins or rivets 22 and holes 21 reversed. In the lower half of the strip, the holes are designated 21' and the rivets are designated 22'. Above the mid-point of the strip 20 each recess 23 has one pin or rivet 22 and two holes 21. Below the mid-point of each strip 20, each recess 23' has two pins or rivets 22' and one hole 21'. When inverted, the rivets 22' register with the holes 21, and the rivets 22 register with the holes 21'. For this purpose, rivets are used, which are provided with countersunk heads and are inserted into countersunk sections 25 of the connecting holes 21. After the strip 20 is attached to the mask part 10, it forms a very wide and flat seal on the side parts. Guide grooves 26, which are used to the extent that the strips can later be inserted flat between the guide rails 31 of the connecting strip 30 shown in FIGS. 3A and 3B, are placed on the upper and lower edges of the strips 20. Retaining grooves 27 are inserted into the edges of the strips 20, which lie on the outside and serve for the later use of a clamp for the holding together of the groups of strips. As shown in FIG. 6, the strips 20 are connected to the strip 30 with spacing strips 28 which are selected from a group of spacing strips of various widths so as to provide adjustment of the relative positions of the marks parts.

Figures 4A, 4B:
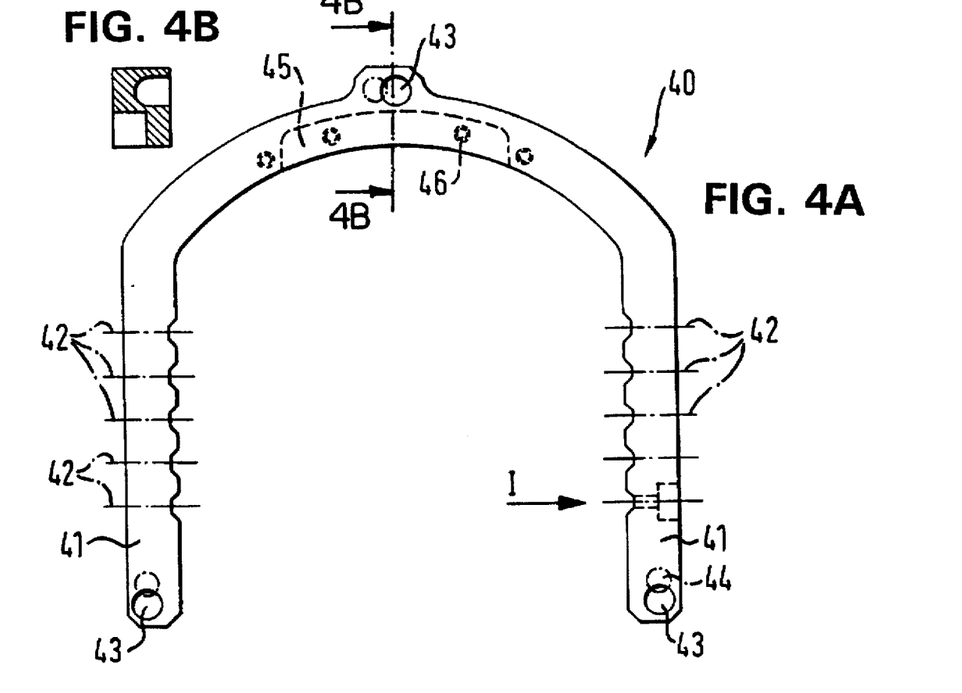
FIG. 4A shows a top view of a head ring serving as a reference system with schematically shown attachment means for the connecting strip shown in FIG. 3 and treatment apparatus to be placed thereon.
FIG. 4B is a local sectional view taken on the line IV—IV of FIG. 4A.

FIG. 3 shows the top view (left) and side view (right) of a connecting strip 30, which makes it possible to connect the individual mask parts with one another by means of the strips. The connecting strip consists of a material with excellent bending strength and tensile strength, especially of a metal or light metal material or of a GFK (glass-plastic reinforced plastic) or CFK (carbon-fiber reinforced plastic) material. The essential components of this connecting strip 30 are the guide rails 31, the generally rectangular rail body 32, and the coupling shoulder 33 arranged on this body, with which the connecting strip 30 is coupled to a reference system, in this case a head ring 40 (FIG. 4A). If the connecting strip 30 is attached to the head ring 40, e.g., by means of a screw connection, the strips 20 attached to the mask parts 11, 13, 14 can be applied flat onto the surfaces 34 and 35 of the connecting strip 30, in that the strips are inserted by inserting the groove 26 into the corresponding guide formed by the rails 31 and are pushed until they stop. The shape of the guide rails 31 and the shape of the groove 26 corresponding to these thus prevent the strips 20 from jamming. On its outside, the connecting strip 30 also has two retaining grooves 36 corresponding to the retaining grooves 27 in position and size, since it must also likewise be clamped to fix the mask.

The connecting strip 30 is designed for coupling onto the head ring 40 shown in FIG. 4. The connecting strip is applied, from the inside, in the arrow direction I (see FIG. 3B and FIG. 4A) with the coupling shoulder 33 to a throughhole in one of the longitudinal legs 41 and it is coupled to this leg, e.g., by means of a knurled screw. In this case, each of the longitudinal legs has several throughholes 42 in order to be able to guarantee the adaptation to various anatomical conditions. Upon application of the connecting strip 30 in the arrow direction I, this would project horizontally from the plane of projection in the view shown in FIG. 4, while the guide rails 31 extend inwards along the direction defined by the longitudinal legs 41. To arrange various surgical or radiation-therapy auxiliary aids, blind holes 43 with seals 44 are provided on the ends of the longitudinal legs 41 and on the crown of the head ring 40. In addition, an attachment recess 45 with tapholes 46 inserted therein is located in the periphery of the crown of the head ring 40.

Figure 5A:
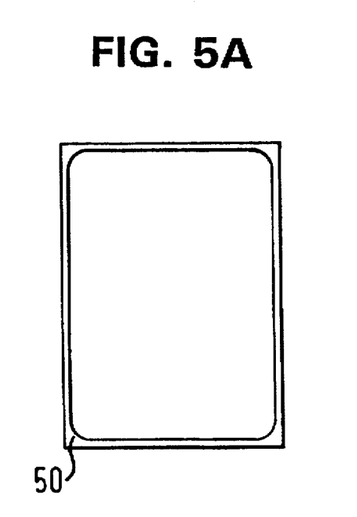
FIG. 5A shows a rear view of a holder for a support for the back of the head for attachment to a head ring according to FIG. 4.
Figure 5B:
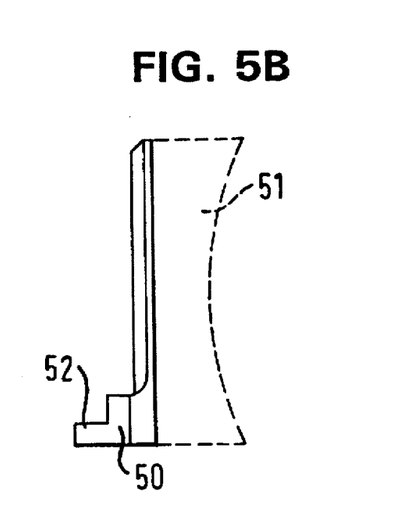
FIG. 5B shows a side view of the holder.

FIGS. 5A and 5B show a head support holder 50, which supports a head support 51 made of plastic (shown in dashed line) for the back of the head of a patient. The head support holder 50 is attached to the head ring 40 by means of the attachment shoulder 52 adapted to the attachment recess 45, while a head support 51 arranged on its surface, whose contour is adapted to the back of the head of the patient, supports this and the rear part of the mask from behind in the head ring.

It can be seen from the perspective view in FIG. 6 how the device according to the present invention, in which a mask has been adapted to the contours of a patient, appears as a completely assembled part. The entire device is held together mainly by the head ring 40; the support for the back of the head 50, 51 is attached to the head ring in the area of the back of the head. On the two side legs of the head ring 40, the two connecting strips 30 are coupled to two opposite throughholes 42. Both the mask parts 10, 13 and the spacing strip 28 are inserted into the guide rails 31 of the connecting strips 30. The groups of strips, consisting of the strips 20, the spacing strip 28 and the connecting strip 30, are held together by means of clamps 29. These clamps 29 are each adapted to the width of the spacing strip 28. When removing these clamps, the two front mask parts 10, 13 are pulled off forwards out of the guides 31 without problems.

By means of an operating sequence for applying and shaping the device according to the present invention, its function should become even clearer below with reference to FIG. 4A through FIG. 8.

First, the head support holder 50 is attached to the crown of the head ring 40 and secured by means of screws to be inserted into the tapholes 46. A head support 51, consisting of plastic, is located on the head support holder. A mask rear part 10, which is provided with two strips 20, is applied to two connecting strips 30 and attached with clips. This takes place on the side of the connecting strip, which has the shorter extension of the guide rails 31, that is, using glued-on attachment extensions with the glue side in the direction of the connecting strip. The guide rails 31 are now coupled via their coupling shoulders 33 to opposite suitable throughholes 42 of the longitudinal legs 41 of the head ring 40 and firmly screwed there by means of a knurled screw 47 at a position indicated by the arrow I in FIG. 4A.

At this time, the thermoplastic material parts must be in the heated, i.e., soft state.

The patient now lies the back of his head into the rear part of the mask and thus also onto the head support and thereby first shapes the rear contours of his mask. While the mask is hardening, the clips remain as a support on the connecting strips 30 and the strips 20.

After the rear mask part has been shaped and hardened, a spacing strip, which is of the same length and depth as the strips 20 and is provided with the same guide grooves on the upper edges, can now first be pushed into the longer section, extending forwards, of the guide which is formed from the rails 31. The width of this spacing strip can later be varied by replacement with another in order to guarantee the function of the dimensional adaptation of the mask according to the present invention. The fixation strips 13 and 14, arranged with their side parts on a strip 20, are now each heated in hot water, i.e., softened, and shaped over the forehead and the upper lip of the patient, whereby the two strips 20, arranged on the side edges, are again pushed into the guides, which are each formed from the two rails 31 of the two connecting strips 30. Thus, the two strips 20 for both fixation strips 13 and 14 come to lie above the spacing strip between the guide rails. It must be guaranteed here that they lie flat. During the hardening, attachment clips are again applied around the now present group of strips.

In connection hereto, a section for the bridge of the nose can be prepared from a thermoplastic material, whose upper end is connected with the not-yet-hardened fixation strip for the forehead and whose lower end is adapted, in the soft state, to the root of the nose of the patient to thus provide a broader point of support and fixation for the head after the hardening of the strip.

Finally, a mask front part 10, which is provided with strips 20 on its sides, is heated and thus softened. This mask front part is applied over the face of the patient so that the recess 12 causes the mouth area of the patient to remain open. The front mask part 10 is made of thermoplastic material, which is perforated in a netlike manner, and thus, it guarantees that the patient can breathe through the nose and see through the gaps in the net during the application of this mask part 10. During the shaping procedure, the strips 20 on the side of the front mask part 10 are again inserted into the guide, formed from the rails 31, and come to lie on the strips 20 for the fixation strips 13 and 14.

The retaining grooves 27 of all strips 20 inserted into the guide rails and into the retaining groove 36 of the connecting strip 30 come to lie aligned with one another between the guide rails 31 during the insertion procedure and thus represent a constant groove, into which a clamp 29 can be inserted in a locking manner for the attachment of all strips 20 and thus of the mask parts to one another as well as with the connecting strip 30. Recesses on the outside of each of the outer strips 20 of the mask front part and rear part are used here to attach the clamp clasps. In the first place, the clamps 29 are designed in their size in such a way that they are appropriate for the spacing strip 28 used first. Sets of clamps of various sizes can be provided for spacing strips of various widths, so that a sufficient attachment of the groups of strips and thus of the mask parts is always guaranteed, and according to the present invention, it is possible to adjust the pressure or the spacing at any time with a firm but rapidly detachable fit.

Especially suitable thermoplastic materials for the mask parts are polyester, especially oxepanone or polycaprolactone; a suitable material is marketed under the name OPTI-MOLD & EZ-MOLD supplied by WFR/Aquaplast Corporation, Wyckoff, N.J.

We claim:

1. For noninvasive, stereotactic immobilization of a head in reproducible position in a firm reference system, said reference system comprising a head ring having a pair of support legs, said legs, adapted to be positioned at opposite sides of the head of a specific patient, a mask comprising a plurality of separate parts capable of assuming a given conformation, a first of said parts being adapted to be conformed to and to cover the anatomical contours of a first area of the specific patient's head, a second of said parts being adapted to be conformed to and to cover the anatomical contours of a second area of the specific patient's head which is not covered by the first of said parts, and means for connecting the mask parts with one another, said connection means also connecting the connected mask parts to the reference system, wherein said connection means comprises a pair of support strips for each mask part, said support strips adapted to be adjustably mounted on the pair of support legs to position the first of said parts to overlie the first area of the patient's head and to position the second of said parts to overlie the second area of the patient's head, and a pair of connecting strips mounting said support strips for adjusting the position of the mask parts relative to one another, and adjusting the position of the position of the mask parts relative to said reference system to thereby separately adjust the pressures applied to the first and second areas by said first and second mask parts.

2. Device in accordance with claim 1, characterized in that the mask parts consist of a thermoplastic material that does not adhere to skin or hair.

3. Device in accordance with claim 2, characterized in that the mask parts consist at least partially of a thermoplastic material that is designed as permeable to air.

4. Device in accordance with claim 1, wherein said first part is multilayered and conforms to front areas of the head and the second part conforms to a rear area of the head, said connection means adapted to accurately position and reposition the head of the specific patient with adjustable pressure between the second part and the multilayered first part and position of the head relative to said reference system.

5. Device in accordance with claim 4, characterized in that said multilayered first part has one layer with a section which consists of a thermoplastic material and conforms to the root of the nose of the patient.

6. Device in accordance with claim 1, wherein said mask parts are recessed in the areas of the mouth of the patient and of the neck.

7. Device in accordance with claim 1, wherein said pairs of support strips and connecting strips are arranged parallel to each other on the opposite sides of the head of the patient, including a mechanical connector adapted to connect a strip of one of said pairs on each side of the head of the patient with the head ring of the reference system.

8. Device in accordance with claim 7, wherein the mask parts have longitudinal edges extending parallel to each other on opposite sides of the head, said support strips being attached to said longitudinal edges, said connecting strips including spacing strips of various widths adapted to be selectively placed between the support strips, said mechanical connector having guides for adjustably supporting the support strips to allow additional spacing strips of various widths to be placed between the support strips, and by the variation in width of the spacing strips, allowing the position of the mask parts to be adjusted relative to one another.

9. Device in accordance with claim 1, including a detachable support for the back of the head arranged between the support legs of the reference system for supporting the back of the head of the patient.

10. For noninvasive, stereotactic immobilization of a head in reproducible position in a firm reference system, said system comprising a head ring having a pair of support legs adapted to be positioned at opposite sides of the head of a specific patient, a mask comprising a plurality of separate parts capable of assuming a given conformation, each of said parts being adapted to be conformed to the anatomical contours of the specific patient's head, said mask parts having longitudinal edges extending parallel to each other on opposite sides of the head, and connection means for connecting the mask parts with one another, said connection means also connecting the connected mask parts to the reference system, said connection means comprising a pair of support strips for each mask part, said support strips being attached to said longitudinal edges and adapted to be adjustably mounted on the pair of support legs, said connection means including spacing strips mounted between said support strips for adjusting the position of said separate mask parts relative to one another, said pairs of support strips and said spacing strips being arranged parallel to each other on the opposite sides of the head of the patient, said connection means including a mechanical connector adapted to connect said support strips and said spacing strips on each side of the head of the patient with the head ring of the reference system, said mechanical connector having guides for adjustably supporting the support strips to allow additional spacing strips of various widths to be placed between the support strips, and by the variation in width of the spacing strips, allowing the position of the mask parts to be adjusted relative to one another, said mechanical connector including clamps adapted to the width of the combined spacing strips and support strips, said clamps being applied across the widths of the combined strips to releasably attach the strips to each other.

* * * * *

UNITED STATES PATENT AND TRADEMARK OFFICE
CERTIFICATE OF CORRECTION

PATENT NO. : 5,702,406
DATED : December 30, 1997
INVENTOR(S) : Stefan Vilsmeier, et. al.

It is certified that error appears in the above-identified patent and that said Letters Patent is hereby corrected as shown below:

Column 6, line 30, after "pins" insert --or--.

Signed and Sealed this

Second Day of June, 1998

Attest:

BRUCE LEHMAN

Attesting Officer

Commissioner of Patents and Trademarks